United States Patent
Kwon et al.

(10) Patent No.: US 6,949,682 B2
(45) Date of Patent: Sep. 27, 2005

(54) CINNAMALDEHYDE DERIVATIVES INHIBITING GROWTH OF TUMOR CELL AND REGULATING CELL CYCLE, PREPARATIONS AND PHARMACEUTICAL COMPOSITIONS THEREOF

(75) Inventors: Byoung-Mog Kwon, Taejon (KR); Kwang-Hee Son, Taejon (KR); Dong Cho Han, Taejon (KR); Sangku Lee, Taejon (KR); Jong Han Kim, Kyungsangnam-do (KR); Sung-Gyu Choi, Taejon (KR); Mi-Young Lee, Kangwon-do (KR); Sun Bok Jeon, Choongchungbook-do (KR)

(73) Assignee: Korea Research Institute of Bioscience and Biotechnology, Taejon (KR)

( * ) Notice: Subject to any disclaimer, the term of this patent is extended or adjusted under 35 U.S.C. 154(b) by 14 days.

(21) Appl. No.: 10/857,756

(22) Filed: May 28, 2004

(65) Prior Publication Data

US 2004/0254196 A1 Dec. 16, 2004

(30) Foreign Application Priority Data

Jun. 10, 2003 (KR) .............................. 10-2003-0037198

(51) Int. Cl.$^7$ .......................... C07C 45/68; A61K 31/11
(52) U.S. Cl. ...................... 568/433; 568/441; 514/699; 514/705
(58) Field of Search ................................. 568/433, 441; 514/699, 705

(56) References Cited

PUBLICATIONS

Bergens et al. Homogeneous Catalysis: Catalytic Intamolecular Conversion of 1,4–Dialdehydes to gamma–Lactones. Organometallics, 1990, 9, p 566–571.*
Gendy et al. Synthesis of 1,4–Diaryl–2,3–diformylbutadienes. Synthesis, 1980, 11, p898–899.*
Peter L. Toogood, Progress Toward the Development of Agents to Modulate the Cell Cycle, Current Opinion in Chemical Biology 2002, 6:472–478 (2002 Elsevier Science Ltd.).
Marcos Malumbres, et al., To Cycle or not to Cycle: A Critical Decision in Cancer, Nature, vol. 1 Dec. 2001, Reviews 222–231 (2001 Nature Publishing Group).

* cited by examiner

Primary Examiner—Johann Richter
Assistant Examiner—Sikarl A. Witherspoon
(74) Attorney, Agent, or Firm—Muserlian, Lucas & Mercanti, LLP

(57) ABSTRACT

The present invention relates to cinnamaldehyde derivatives inhibiting growth of tumor cell and regulating cell cycle, the method for preparation and the pharmaceutical composition thereof. The cinnamaldehyde derivatives of the present invention can be effectively used as a cell cycle regulator or a cancer cell growth inhibitor, since it has an ability to regulate cell cycle by holding the cells in G2/M stage of the cell division and has activity to inhibit cancer cell growth.

5 Claims, No Drawings

CINNAMALDEHYDE DERIVATIVES INHIBITING GROWTH OF TUMOR CELL AND REGULATING CELL CYCLE, PREPARATIONS AND PHARMACEUTICAL COMPOSITIONS THEREOF

This patent application claims the benefit of priority from Korean Patent Application No. 10-2003-0037198 filed Jun. 10, 2003 the contents of which are incorporated herein by reference.

BACKGROUND OF THE INVENTION

1. Field of the Invention

The present invention relates to cinnamaldehyde derivatives represented by formula 1, process for preparation and pharmaceutical compositions thereof. Particularly, the present invention relates to cinnamaldehyde derivatives inhibiting growth of tumor cell and regulating cell cycle, the method for preparation thereof and the pharmaceutical composition as tumor cell growth inhibitor or cell cycle regulator.

<Formula 1>

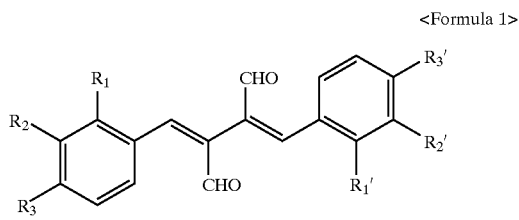

(wherein, $R_1$, $R_1'$, $R_2$, $R_2'$, $R_3$ and $R_3'$ are described in the below.)

2. Description of the Prior Art

Proliferation, differentiation and apoptosis are the major phenomena to keep a life. In order for cell to function normally, cellular proliferation, differentiation, and apoptosis are regulated by an elaborate intracellular and intercellular signal transduction system. That is, once cells are given a signal from outside, the signal is transferred to cellular clock by signaling proteins (PLC, PKC, Shc, Grb2, Raf, MAPK, MEK, etc.) and signaling messengers (GTP, cAMP, etc.). Any abnormality in the process causes diseases such as cancer.

Cell cycle is composed of following stages; Gap(G1), DNA synthesis(S), Gap2(G2) and Meiosis(M). In addition to the stages, when cells have been under the condition of having lower concentration of a growth factor for a long while, the cells get into the resting stage(Go), in which cell growth is stopped.

In cell cycle, a very complicated network, so called 'check point', makes the cell clock move properly in the order of G1-S-G2-M. The obstruction of the regulating mechanism of the check point results in uncontrolled cell growth.

If signal transduction from outside of the nucleus is smooth and nutritional condition is good, cells become larger in stage G1 and then entered cell cycle. Cell cycle goes into action in G1 check point which is named as start point in yeast cells, and restriction point in mammalian cells. After passing through the stage, if there is no specific obstruction, cells go through the 4 stages automatically, leading to the replication of genomes and differentiation. The procedure, especially in mammalian cells, is precisely explained hereinafter. The stage G1 having the check point is a preparatory stage for making new cells. At this time, enough growth factors and nutrition should be given to cells. Otherwise, cell cycle is stopped and cells go into the stage Go with no more growth. However, cell cycle progresses to the stage S under the supply of various growth factors and nutrition. At this time, replication of genome is carried out, two copies of chromosomes are produced, and various factors in cytoplasm are duplicated as well in order for a cell to be differentiated into two individual cells. After passing through the stage S, cells go into the stage G2, which can be said as the second check point. During the stage G2, DNA replication is regulated and completed, and entry to meiosis (M stage) is prepared. Lots of factors essential for the construction of a cell are generated in this stage. After the generation of all the required factors for the cell division, cells progress to the stage M, the stage in which actual cell proliferation occurs. The stage M has the shortest period among stages. In this stage, the duplicated genome is separated and each part moves to both poles, resulting in two daughter cells. All the stages are required in order for a cell to divide into two cells, so that they are very important for continuing the life of a cell. Thus, the studies on cell cycle and the development of a regulator of the cell cycle are prerequisite for the studies on mechanisms of cell growth and for the development of a preventive or a treatment agent for cancer caused by the abnormality of cell cycle (*Nature Review Cancer*, 2001, 1, 222–231).

As mentioned above, mammalian cell growth can be regulated by controlling the first check point in G1 stage or the second check point in G2/M stage. The abnormal progress of the first or the second check point is involved in cellular ageing or the development of cancer. And cycline D (D1, D2, D3, etc.) plays an important role in those check points. Cycline D regulates the enzyme activity by being combined with cycline dependant kinases (CDK; CDK2, CDK4, CDK6), and is also deeply involved in the regulation of whole cell cycle by CDC25 which functions to remove phosphate group of a phosphorylated protein. Based on that founding, it is no wonder that various cell cycle regulators have been good candidates for the development of a treatment agent for intractable diseases such as cancers. (*Current Opinion in Chemical Biology*, 2002, 6, 472–278).

Thus, the present inventors have disclosed that the novel cinnamaldehyde derivatives could block the G2/M selectively and have completed the invention by confirming that the cinnamaldehyde derivatives could be effectively used as a cell cycle regulator and as an inhibitor for abnormal cell growth of cancer cells.

OBJECT OF THE INVENTION

It is an object of the present invention to provide cinnamaldehyde derivatives used as tumor cell growth inhibitor or cell cycle regulator by selectively holding cells in G2/M of cell cycle.

It is another object of the present invention to provide the method for preparation the cinnamaldehyde derivatives.

It is a further object of the present invention to provide the pharmaceutical compositions comprising cinnamaldehyde derivatives as effective ingredient.

SUMMARY OF THE INVENTION

The present invention provides cinnamaldehyde derivatives represented by formula 1.

<Formula 1>

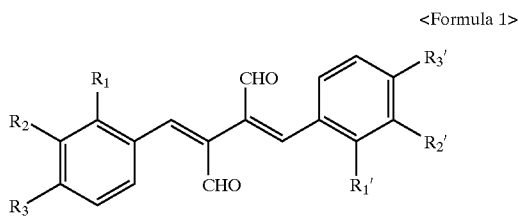

(wherein, $R_1$ and $R_1'$ are same, $R_2$ and $R_2'$ are same, and $R_3$ and $R_3'$ are same.

$R_1$, $R_2$ and $R_3$ are independent each other, hydrogen, hydroxy, halogen, $C_1$~$C_4$ alkyl, $C_1$~$C_4$ alkoxy,

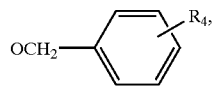

$OCOR_5$, N-methylpiperazine;

$R_4$ is hydrogen, nitro, $C_1$~$C_4$ alkoxy;

$R_5$ is $C_1$~$C_4$ alkyl, phenyl, phenyl substituted by halogen.)

The present invention preferably provides compounds represented by the followings.

1) 2,3-bis-benzylidenesuccinaldehyde;
2) 2,3-bis-(2-fluorobenzylidene)succinaldehyde;
3) 2,3-bis-(2-chlorobenzylidene)succinaldehyde;
4) 2,3-bis-(2-bromobenzylidene)succinaldehyde;
5) 2,3-bis-(2-methoxybenzylidene)succinaldehyde;
6) 2,3-bis-(3-chlorobenzylidene)succinaldehyde;
7) 2,3-bis-(4-hydroxy-3-methoxybenzylidene) succinaldehyde;
8) 2,3-bis-(3,4-dimethoxybenzylidene)succinaldehyde;
9) 2,3-bis-(4-chlorobenzylidene)succinaldehyde;
10) 2,3-bis-(4-hydroxy-benzylidene)succinaldehyde;
11) 2,3-bis-(4-methyl-benzylidene)succinaldehyde;
12) 2,3-bis-(4-methoxy-benzylidene)succinaldehyde;
13) 2,3-bis-(2-propyloxy-benzylidene)succinaldehyde;
14) 2,3-bis-(2-allyloxy-benzylidene)succinaldehyde;
15) 2,3-bis-(2-isopropyloxy-benzylidene)succinaldehyde;
16) 2,3-bis-(2-benzyloxy-benzylidene)succinaldehyde;
17) 2,3-bis-(2-(4-chlorobenzyloxy)-benzylidene) succinaldehyde;
18) 2,3-bis-(2-(4-bromobenzyloxy)-benzylidene) succinaldehyde;
19) 2,3-bis-(2-(4-nitrobenzyloxy)-benzylidene) succinaldehyde;
20) 2,3-bis-(3-propyloxy-benzylidene)succinaldehyde;
21) 2,3-bis-(3-isopropyloxy-benzylidene)succinaldehyde;
22) 2,3-bis-(3-benzyloxy-benzylidene)succinaldehyde;
23) 2,3-bis-(4-propyloxy-3-methoxy-benzylidene) succinaldehyde;
24) 2,3-bis-(4-isopropyloxy-3-methoxy-benzylidene) succinaldehyde;
25) 2,3-bis-(4-acetyloxy-3-methoxy-benzylidene) succinaldehyde;
26) 2,3-bis-(4-valeryloxy-3-methoxy-benzylidene) succinaldehyde;
27) 2,3-bis-(4-benzoyloxy-3-methoxy-benzylidene) succinaldehyde;
28) 2,3-bis-(4-propyloxy-benzylidene)succinaldehyde;
29) 2,3-bis-(4-isopropyloxy-benzylidene)succinaldehyde;
30) 2,3-bis-(4-valeryloxy-benzylidene)succinaldehyde;
31) 2,3-bis-(4-benzyloxy-benzylidene)succinaldehyde;
32) 2,3-bis-(4-benzoyloxy-benzylidene)succinaldehyde;
33) 2,3-bis-(4-(2-fluorobenzoyloxy)-benzylidene) succinaldehyde;
34) 2,3-bis-(4-(4-bromobenozyloxy)-benzylidene) succinaldehyde;
35) 2,3-bis-(2-(N-methylpiperazine)benzylidene) succinaldehyde;
36) 2,3-bis-(3-(4-chlorobenzyloxy)-benzylidene) succinaldehyde;
37) 2,3-bis-(3-(4-methoxybenzyloxy)-benzylidene) succinaldehyde;
38) 2,3-bis-(4-(4-chlorobenzyloxy)-benzylidene) succinaldehyde; and
39) 2,3-bis-(4-(4-methoxybenzyloxy)-benzylidene) succinaldehyde.

The compound of the present invention shown in the above formula 1 can be effectively used as a cancer cell growth inhibitor or a cell cycle regulator, since it regulates cell cycle by holding a cell in the middle of division in stage G2/M of cell cycle and inhibits the cancer cell growth thereby.

The present invention provides the method for preparation of the cinnamaldehyde derivatives represented by formula 1.

As shown in scheme 1, the cinnamaldehyde derivatives of the present invention are prepared by linear dimerization of benzaldehyde substituted by $R_1$, $R_2$ and $R_3$(represented by formula I). Particularly, as shown in scheme 1, the cinnamaldehyde derivatives(II) of the present invention are prepared by linear dimerization of benzaldehyde substituted by $R_1$, $R_2$ and $R_3$(represented by formula I) in the presence of 2,5-dimethoxytetrahydrofuran, potassium acetate, acetic acid and water.

<scheme 1>

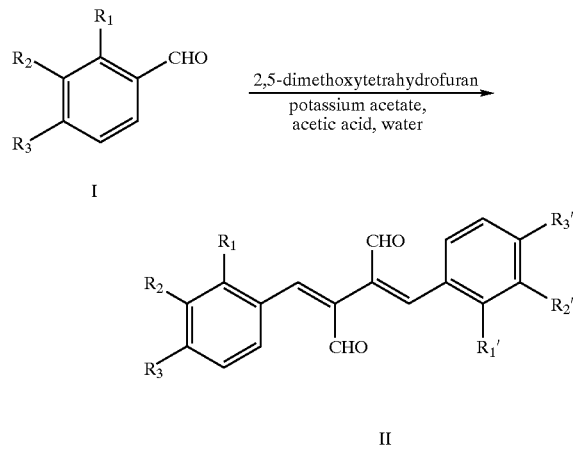

(wherein, $R_1$, $R_1'$, $R_2$, $R_2'$, $R_3$ and $R_3'$ are described in the formula 1)

The benzaldehydes substituted with $R_1$, $R_2$ and $R_3$(represented by formula I) are used as commercially available formulation. Also, the benzaldehydes substituted with $R_1$, $R_2$ and $R_3$ (represented by formula I) are prepared by reacting alkylating agent to benzaldehyde substituted with activating substitutent such as halogen or hydroxy group in the presence of base, but not is limited to them. As shown in example 13, for example, 2-propyloxybenzaldehyde(I) was prepared by reacting 1-iodopropane(alkylating agent) to 2-hydroxybenzaldehyde substituted with hydroxyl group in the presence of potassium carbonate(base).

Also, the cinnamaldehyde derivatives(II) of the present invention are prepared by dimerizing the benzaldehyde (by linear dimerization) and transforming $R_1$, $R_1'$, $R_2$, $R_2'$, $R_3$ and $R_3'$. Then, $R_1$, $R_1'$, $R_2$, $R_2'$, $R_3$ and $R_3'$ are transformed by reacting the dimerized product to alkylating agent in the presence of base, but not is limited to them. As shown in example 23, for example, 2,3-bis-(4-hydroxy-3-methoxybenzylidene) was prepared by linear-dimerizing vaniline in the presence of 2,5-dimethoxytetrahydrofuran, potassium acetate, acetic acid and water, thereafter the dimerized product reacted 1-iodopropan(alkylating agent) in the presence of potassium acetate(base) to transform hydroxy group to propyloxy group.

Also, the present invention provides the pharmaceutical compositions as tumor cell growth inhibitor or cell cycle regulator, comprising cinnamaldehyde derivatives as effective ingredient.

The pharmaceutical compositions comprising cinnamaldehyde derivatives as effective ingredient can be administered through various administration routes such as oral or parenteral formulations in practically clinical testing. Also, the pharmaceutical compositions can be used as medicine.

The cinnamaldehyde derivatives of the present invention can be administered to a human body through various formulations.

The pharmaceutical compositions of the present invention contain further the pharmaceutically acceptable carrier. More particularly, the pharmaceutically acceptable carrier is any of the standard pharmaceutical carriers used in the known formulations, such as sterile solution, tablet, coating tablet and capsule. Conservatively, the carrier is selected from the group of excipient such as starch, milk, glucose, specific clay, gelatin, stearic acid, talc, vegetable oil or fat, gum, glycol, the other known excipients, flavoring agents, pigment additives and other components.

Pharmaceutical compositions as tumor cell growth inhibitor or cell cycle regulator, containing cinnamaldehyde derivatives of the formula 1 according to the present invention is administered, but not is limited, through conservative routes such as oral, intravenous injection, intramuscular injection, transdermal administration. For example, the cinnamaldehyde derivatives according to the present invention can be administered to a human body through various oral or parenteral formulations in practically clinical testing. Formulations are prepared by using available additives such as packing agents, bulking agents, binding agents, disintegrants and surfactants, or excipients. Solid formulations for oral administration are provided into various forms including tablets, pills, powders, granules and capsules. Solid formulations are prepared by mixing one or more compounds selected from the group consisting of cinnamaldehyde derivatives of the formula 1, and at least one excipient which is selected from the group consisting of starch, calcium carbonate, sucrose or lactose, and gelatin. Also, lubricants such as magnesium stereate talc can be used together with simple diluting agent. Liquid formulations for oral administration are provided into suspension, solution, emulsion and syrup. Various excipients, for example, moistening agent, sweeting agent, aromatic agent and preservative can be included in liquid formulations, together with simple diluting agent, commercially available, such as water, or liquid paraffin.

Also, the pharmaceutical composition of the present invention can be administered to a human body parenterally. Parenteral administration is carried out by hypodermic injection, intravenous injection or intramuscular injection. The formulation for parenteral administration is prepared by mixing the cinnamaldehyde derivatives with stabilizing agents or buffering agents in water, formulating solution or suspension and preparing an unit dosage form, such as ample or vial.

In accordance with the present invention, cinnamaldehyde derivatives of formula 1 are contained in the pharmaceutical compositions in broad ranges. The dose of the medically effective component in accordance with the present invention is selected according to absorptivity of the active component in vivo, activity, excretion rate, age, sex and state of the patients, seriousness of disease under treatment. Generally, the effective component can be administered to a body one time or many times a day, preferably 10~20 mg, more preferably 5~10 mg. Accurate dose, administration route and frequency of the above preparation are dependant on property of the preparation, weight or state of the administrative human, and property of specific derivatives.

DETAILED DESCRIPTION OF THE INVENTION

The present invention will be explained in more detail with reference to the following examples. However, the following examples are provided only to illustrate the present invention, and the present invention is not limited to them.

EXAMPLE 1

2,3-bis-benzylidenesuccinaldehyde

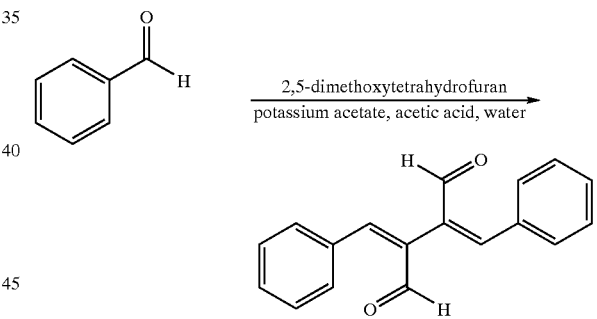

15.9 ml of benzaldehyde (150 mmol) was added to the 250 ml round-bottomed flask. Thereafter 10 ml of 2,5-dimethoxytetrahydrofuran(75 mmol), 10 g of potassium acetate (100 mmol), 5 ml of acetic acid (80 mmol) and 5 ml of water were added to the flask. The reaction mixture was refluxed at 110° C. for 12 hours. After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography, to give the title compound as a yellow crystal (yield: 10%)

mp: 109~110° C.

$R_f$: 0.5 (Hexane:Ethyl acetate=6:4).

$^1$H-NMR(CDCl$_3$/TMS) (ppm): δ 1.08 (t, 6H, —CH$_3$, J=7.5 Hz), 1.86(m, 4H, —CH$_2$—, J=7.5 Hz), 3.96(m, 4H, CH$_2$—, J=6.6 Hz), 6.73~7.44(m, 8H), 8.12(s, 2H, CH=C—), 9.66(s, 2H, CH=O).

EXAMPLE 2~12

In the Example 1, benzaldehyde substituted with R$_1$, R$_2$ and R$_3$ shown in table 1 was used in place of benzaldehyde, and the same procedure as the example 1 was accomplished.

EXAMPLE 2

2,3-bis-(2-fluorobenzylidene)succinaldehyde mp: 141~142° C.

Rf=0.35 (Hexane:Ethylacetate=6:4)

$^1$H-NMR(CDCl$_3$/TMS) (ppm): δ 7.00~7.08(d, 4H$_{arom}$), 7.29~7.41(m, 4H$_{arom}$), 7.88(s, 2H, CH=C—), 9.69(s, 2H, CH=O)

EXAMPLE 3

2,3-bis-(2-chlorobenzylidene)succinaldehyde mp: 177~178° C.

Rf=0.31 (Hexane:Ethylacetate=6:4)

$^1$H-NMR(CDCl$_3$/TMS) (ppm): δ 7.13~7.28(m, 8H$_{arom}$), 7.83(s, 2H, CH=C—), 9.73(s, 2H, CH=O)

EXAMPLE 4

2,3-bis-(2-bromobenzylidene)succinaldehyde mp: 194~195° C.

Rf=0.29 (Hexane:Ethylacetate=6:4)

$^1$H-NMR(CDCl$_3$/TMS) (ppm): δ 7.12~7.46(m, 8H$_{arom}$), 7.73(s, 2H, CH=C—), 9.74(s, 2H, CH=O)

EXAMPLE 5

2,3-bis-(2-methoxybenzylidene)succinaldehyde mp: 163~164° C.

Rf=0.25 (Hexane:Ethylacetate=6:4)

$^1$H-NMR(CDCl$_3$/TMS) (ppm): δ 3.85(s, 6H, —OCH$_3$), 6.76~7.41(m, 8H$_{arom}$), 8.07(s, 2H, CH=C—), 9.65(s, 2H, CH=O)

EXAMPLE 6

2,3-bis-(3-chlorobenzylidene)succinaldehyde mp: 107~108° C.

Rf=0.31 (Hexane:Ethylacetate=6:4)

$^1$H-NMR(CDCl$_3$/TMS) (ppm): δ 7.24~7.42(m, 8H$_{arom}$), 7.64(s, 2H, CH=C—), 9.67(s, 2H, CH=O)

EXAMPLE 7

2,3-bis-(4-hydroxy-3-methoxy-benzylidene) succinaldehyde mp: 177~178° C.

Rf=0.15 (Hexane:Ethylacetate=4:6)

$^1$H-NMR(CDCl$_3$/TMS) (ppm): δ 3.75(s, 6H, —OCH$_3$), 5.92(s, 2H, —OH), 6.85~7.16(m, 6H$_{arom}$), 7.63(s, 2H, CH=C—), 9.63(s, 2H, CH=O)

EXAMPLE 8

2,3-bis-(3,4-dimethoxybenzylidene)succinaldehyde mp: 149~150° C.

Rf=0.2 (Hexane:Ethylacetate=4:6)

$^1$H-NMR(CDCl$_3$/TMS) (ppm): 6.73(s, 6H, —OCH$_3$), 3.88(s, 6H, —OCH$_3$), 6.81~7.21(m, 6H$_{arom}$), 7.65(s, 2H, CH=C—), 9.65(s, 2H, CH=O)

EXAMPLE 9

2,3-bis-(4-chlorobenzylidene)succinaldehyde mp: 172~173° C.

Rf=0.31 (Hexane:Ethylacetate=6:4)

$^1$H-NMR(CDCl$_3$/TMS)(ppm): δ 7.27~7.44(m, 8H$_{arom}$), 7.66(s, 2H, CH=C—), 9.65(s, 2H, CH=O)

EXAMPLE 10

2,3-bis-(4-hydroxy-benzylidene)succinaldehyde mp: 244~246° C.

Rf=0.25 (Hexane:Ethylacetate=6:4)

$^1$H-NMR(CDCl$_3$/TMS) (ppm): δ 6.73(dd, 4H), 7.48(dd, 4H), 7.73(s, 2H, CH=C—), 9.57(s, 2H, CH=O)

EXAMPLE 11

2,3-bis-(4-methyl-benzylidene)succinaldehyde mp: 177~178° C.

Rf=0.5 (Hexane:Ethylacetate=6:4)

$^1$H-NMR(CDCl$_3$/TMS) (ppm): δ 2.32(s, 6H, —CH$_3$), 7.11(dd, 4H), 7.43(dd, 4H), 7.67(s, 2H, CH=C—), 9.64(s, 2H, CH=O)

EXAMPLE 12

2,3-bis-(4-methoxy-benzylidene)succinaldehyde mp: 207~207° C.

Rf=0.23 (Hexane:Ethylacetate=6:4)

$^1$H-NMR(CDCl$_3$/TMS) (ppm): δ 3.79(s, 6H, —OCH$_3$), 6.83(dd, 4H), 7.51(dd, 4H), 7.64(s, 2H, CH=C—), 9.63(s, 2H, CH=O)

EXAMPLE 13

2,3-bis(2-propyloxy-benzylidene)succinaldehyde

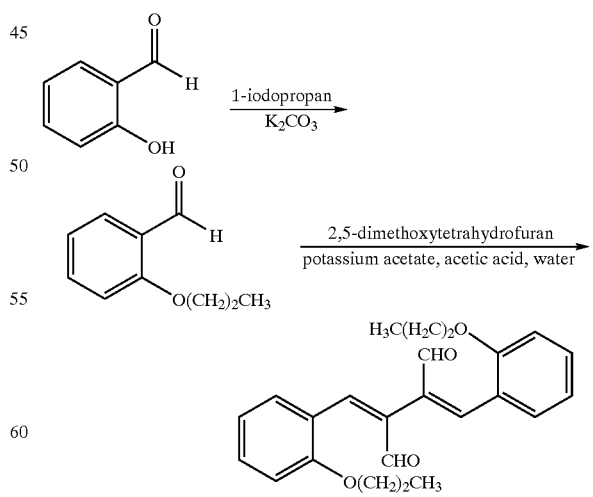

(Step 1): Preparation of 2-propyloxy benzaldehyde 6.1 g of 2-hydroxybenzaldehyde (50 mmol) was added to the 250 ml round-bottomed flask, 50 ml of acetonitrile was added therein. Thereafter, 8.28 g of potassium carbonate (60 mmol) and 9.35 g of 1-iodopropan (55 mmol) were added therein. The reaction mixture was refluxed at 85° C. for 12 hours.

After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography. Substitution of propyl group was confirmed by hydrogen NMR.

(Step 2): Preparation of 2,3-bis(2-propyloxy-benzylidene) succinaldehyde 5 g of 2-propyloxy benzaldehyde (30 mmol) prepared in the above step 1 was added to the 250 ml round-bottomed flask. Thereafter, 2 ml of 2,5-dimethoxytetrahydrofuran(15 mmol), 2 g of potassium acetate (20 mmol), 1 ml of acetic acid (16 mmol) and 1 ml of water were added to the flask. The reaction mixture was refluxed at 110° C. for 12 hours. After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography, to give the title compound as a yellow crystal (yield: 10%)

mp: 109~110° C.

$R_f$: 0.5 (Hexane:Ethyl acetate=6:4)

$^1$H-NMR(CDCl$_3$/TMS) (ppm): δ 1.08(t, 6H, —CH$_3$, J=7.5 Hz), 1.86(m, 4H, —CH$_2$—, J=7.5 Hz), 3.96(m, 4H, CH$_2$—, J=6.6 Hz), 6.73~7.44(m, 8H), 8.12(s, 2H, CH=C—), 9.66(s, 2H, CH=O)

EXAMPLE 14~19

In the Example 13, alkylating agent containing $R_1$ shown in table 1 was used in place of 1-iodopropan, and the same procedure as the example 13 was accomplished.

EXAMPLE 14

2,3-bis-(2-allyloxy-benzylidene)succinaldehyde mp: 117~118° C.

Rf=0.46 (Hexane:Ethylacetate=6:4)

$^1$H-NMR(CDCl$_3$/TMS) (ppm): δ 4.57(dd, 4H, CH$_2$—CH), 5.36(q, 4H, CH=CH$_2$), 6.07(m, 2H, C$_H$=CH$_2$), 6.76~7.42(m, 8H$_{arom}$), 8.11(s, 2H, CH=C—), 9.67(s, 2H, CH=O)

EXAMPLE 15

2,3-bis-(2-isopropyloxy-benzylidene)succinaldehyde mp: 109~110° C.

Rf=0.45 (Hexane:Ethylacetate=6:4)

$^1$H-NMR(CDCl$_3$/TMS) (ppm): δ 1.38(dd, 12H, CH$_3$—CH—CH$_3$), 4.58(m. 2H, CH$_3$—CH—CH$_3$), 6.72~7.44 (m, 8H$_{arom}$), 8.10(s, 2H, CH=C—), 9.66(s, 2H, CH=O)

EXAMPLE 16

2,3-bis-(2-benzyloxy-benzylidene)succinaldehyde mp: 120~121° C.

Rf=0.48 (Hexane:Ethylacetate=6:4)

$^1$H-NMR(CDCl$_3$/TMS) (ppm): δ 5.09(dd, 4H, CH$_2$-Arom), 6.76~7.45(m, 18H$_{arom}$), 8.13(s, 2H, CH=C—), 9.65(s, 2H, CH=O)

EXAMPLE 17

2,3-bis-(2-(4-chlorobenzyloxy)-benzylidene) succinaldehyde mp: 186~187° C.

Rf=0.35 (Hexane:Ethylacetate=7:3)

$^1$H-NMR(CDCl$_3$/TMS)(ppm): δ 5.02(dd, 4H, CH$_2$-Arom), 6.70~7.36(m, 16H$_{arom}$), 8.01(s, 2H, CH=C—), 9.56(s, 2H, CH=O)

EXAMPLE 18

2,3-bis-(2-(4-bromobenzyloxy)-benzylidene) succinaldehyde mp: 210~211° C.

Rf=0.4 (Hexane:Ethylacetate=7:3)

$^1$H-NMR(CDCl$_3$/TMS)(ppm): δ 5.07(dd, 4H, CH$_2$-Arom), 6.77~7.54(m, 16H$_{arom}$), 8.08(s, 2H, CH=C—), 9.63(s, 2H, CH=O)

EXAMPLE 19

2,3-bis-(2-(4-nitrobenzyloxy)-benzylidene) succinaldehyde mp: 116~117° C.

Rf=0.4 (Hexane:Ethylacetate=7:3)

$^1$H-NMR(CDCl$_3$/TMS)(ppm): δ 0.31(s, 4H, CH$_2$-Arom), 6.99~8.30(m, 16H, H$_{arom}$), 10.56(s, 2H, CH=O)

EXAMPLE 20

2,3-bis-(3-propyloxy-benzylidene)succinaldehyde

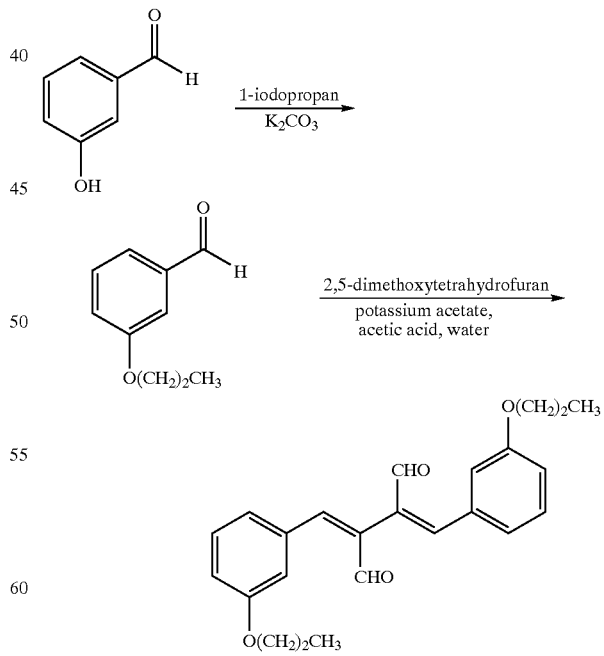

(Step 1): Preparation of 3-propyloxy benzaldehyde 6.1 g of 3-hydroxy benzaldehyde (50 mmol) was added to the 250 ml round-bottomed flask, 50 ml of acetonitrile was added therein. Thereafter, 8.28 g of potassium carbonate (60 mmol) and 9.35 g of 1-iodopropan (55 mmol) were added therein. The reaction mixture was refluxed at 85° C. for 10 hours.

After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography. Substitution of propyl group was confirmed by hydrogen-NMR.

(Step 2): Preparation of 2,3-bis(3-propyloxy-benzylidene)succinaldehyde 5 g of 3-propyloxy benzaldehyde (30 mmol) prepared in the above step 1 was added to the 250 ml round-bottomed flask. Thereafter, 2 ml of 2,5-dimethoxytetrahydrofuran(15 mmol), 2 g of potassium acetate (20 mmol), 1 ml of acetic acid (16 mmol) and 1 ml of water were added to the flask. The reaction mixture was refluxed at 110° C. for 12 hours. After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography, to give the title compound as a brown powder (1 g, yield: 10%)

mp: 93~94° C.

$R_f$: 0.52 (Hexane:Ethylacetate=6:4)

$^1$H-NMR(CDCl$_3$/TMS) (ppm): δ 0.99(t, 6H, —CH$_2$—CH$_3$, J=7.2 Hz), 1.76(m, 4H, CH$_2$—CH$_2$—, J=6.9 Hz), 3.81(m, 4H, CH$_2$—CH$_2$, J=1.2 Hz), 6.88~7.26(m, 8H arom), 7.67(s, 2H, CH═C—), 9.65(s, 2H, CH═O)

EXAMPLE 21~22

In the Example 20, alkylating agent containing R$_2$ shown in table 1 was used in place of 1-iodopropan, and the same procedure as the example 20 was accomplished.

EXAMPLE 21

2,3-bis-(3-isopropyloxy-benzylidene)succinaldehyde mp: 116~117° C.

Rf=0.48 (Hexane:Ethylacetate=6:4)

$^1$H-NMR(CDCl$_3$/TMS) (ppm): δ 1.27(q, 12H, CH—CH$_3$), 4.35~4.43(m, 2H, CH—CH$_3$), 6.86~7.26(m, 8H$_{arom}$), 7.66(s, 2H, CH═C—), 9.65(s, 2H, CH═O)

EXAMPLE 22

2,3-bis-(3-benzyloxy-benzylidene)succinaldehyde mp: 126~127° C.

Rf=0.44 (Hexane:Ethylacetate=6:4)

$^1$H-NMR(CDCl$_3$/TMS) (ppm): δ 4.97(s, 4H, CH$_2$-ph), 6.97~7.38(m, 18H$_{arom}$), 7.51(s, 2H, CH═C—), 9.48(s, 2H, CH═O)

EXAMPLE 23

2,3-bis-(4-propyloxy-3-methoxybenzylidene)succinaldehyde

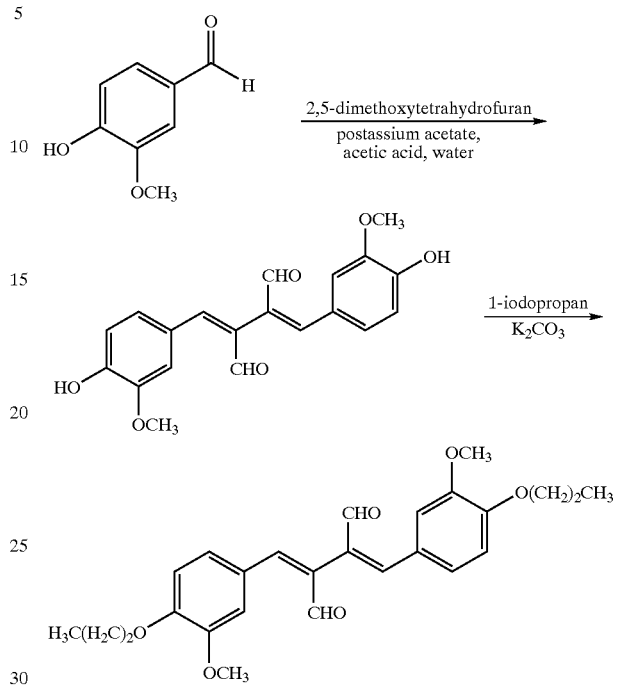

(Step 1): Preparation of 2,3-bis-(4-hydroxy-3-methoxy-benzylidene)succinaldehyde 45.65 g of vaniline (300 mmol) was added to the 250 ml round-bottomed flask. Thereafter, 20 ml of 2,5-dimethoxytetrahydrofuran(150 mmol), 20 g of potassium acetate, 10 ml of acetic acid and 10 ml of water were added therein. The reaction mixture was refluxed at 110° C. for 12 hours.

After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography. Substitution of propyl group was confirmed by hydrogen-NMR.

(Step 2): Preparation of 2,3-bis(4-propyloxy-3-methoxybenzylidene)succinaldehyde 30 mg of 2,3-bis-(4-hydroxy-3-methoxy-benzylidene)succinaldehyde(0.08 mmol) prepared in the above step 1 was added to the 100 ml round-bottomed flask. Thereafter, 30 mg of potassium carbonate(0.18 mmol) and 30 mg of 1-iodopropan(0.18 mmol) were added to the flask. Thereafter, the mixture was stirred at 85° C. for 12 hours. After the termination of the reaction is confirmed with thin layer chromatography, the reaction mixture was filtered to obtain the filtrate. The residue obtained by concentrating the filtrate was purified with silica gel column chromatography to prepare 20 mg of the title compound as yellow powder.

mp: 95~96° C.

$R_f$: 0.15 (Hexane:Ethyl acetate=4:6)

$^1$H-NMR(CDCl$_3$/TMS) (ppm): δ 1.01(t, 6H, —CH$_2$—CH$_3$, J=7.2 Hz), 1.80~1.87(m, 5H, CH$_2$—CH$_3$, J=6.9 Hz), 3.70(s, 6H, —OCH₃), 3.97(t, 4H, —OCH₂—CH₂, J=6.6 Hz), 6.78~7.17(m, 6H), 7.63(s, 2H, CH═C—), 9.64(s, 2H, CH═O)

EXAMPLE 24~27

In the Example 23, alkylating agent containing $R_3$ shown in table 1 was used in place of 1-iodopropan, and the same procedure as the example 23 was accomplished.

EXAMPLE 24

2,3-bis-(4-isopropyloxy-3-methoxy-benzylidene)succinaldehyde mp: 119~120° C.

Rf=0.4 (Hexane:Ethylacetate=4:6)

¹H-NMR(CDCl₃/TMS) (ppm): δ 1.36(d, 12H, CH₃—CH—CH₃), 3.69(s, 6H, —OCH₃), 4.55~4.59(m, 2H, CH₃—CH—CH₃),6.79~7.17(m, 6H$_{arom}$), 7.63(s, 2H, CH═C—), 9.64(s, 2H, CH═O)

EXAMPLE 25

2,3-bis-(4-acetyloxy-3-methoxy-benzylidene)succinaldehyde mp: 149~151° C.

Rf=0.42 (Hexane:Ethylacetate=4:6)

¹H-NMR(CDCl₃/TMS) (ppm): δ 2.30(s, 6H, O═C—CH₃), 3.72(s, 6H, —OCH₃), 7.00~7.14(m, 6H$_{arom}$), 7.68(s, 2H, CH═C—), 9.66(s, 2H, CH═O)

EXAMPLE 26

2,3-bis-(4-valeryloxy-3-methoxy-benzylidene)succinaldehyde mp: gel

Rf=0.3 (Hexane:Ethylacetate=4:6)

¹H-NMR(CDCl₃/TMS) (ppm): δ 0.96(t, 6H, CH₂—CH₃), 1.38~1.51(m, 4H, CH₂—CH₃), 1.64~1.78(m, 4H, CH₂—CH₂), 2.57(t, 4H, OCH₂—CH₂), 3.71(s, 6H, —OCH₃), 6.99~7.14(m, 6H$_{arom}$), 7.27(s, 2H, CH═C—), 9.65(s, 2H, CH═O)

EXAMPLE 27

2,3-bis-(4-benzoyloxy-3-methoxy-benzylidene)succinaldehyde mp: 107~110° C.

Rf=0.45 (Hexane:Ethylacetate=4:6)

1H-NMR(CDCl3/TMS)(ppm): δ 3.73(s, 6H, —OCH3), 7.14~8.82(m, 16Harom), 7.74(s, 2H, CH═C—), 9.69(s, 2H, CH═O)

EXAMPLE 28

2,3-bis-(4-propyloxybenzylidene)succinaldehyde

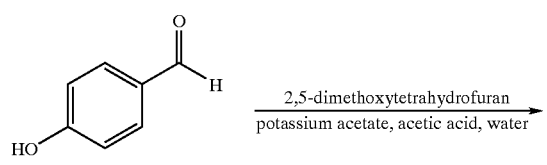

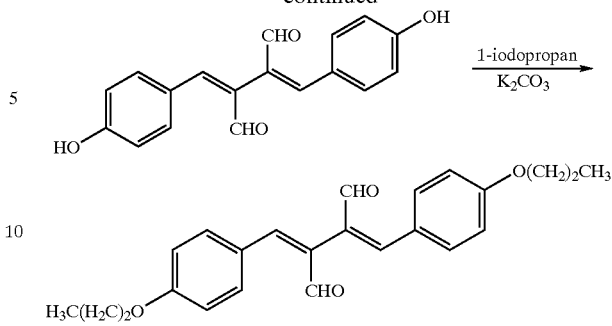

(Step 1): Preparation of 2,3-bis-(4-hydroxybenzylidene)succinaldehyde 3.66 g of 4-hydroxybenzaldehyde (30 mmol) was added to the 250 ml round-bottomed flask. Thereafter, 2 ml of 2,5-dimethoxytetrahydrofuran (15 mmol), 2 g of potassium acetate, 1 ml of acetic acid and 1 ml of water were added therein. The reaction mixture was refluxed at 110° C. for 12 hours.

After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography. Substitution of propyl group was confirmed by hydrogen-NMR.

(Step 2): Preparation of 2,3-bis(4-propyloxy-benzylidene)succinaldehyde 24 mg of 2,3-bis-(4-hydroxy-benzylidene)succinaldehyde (0.08 mmol) prepared in the above step 1 was added to the 100 ml round-bottomed flask. Thereafter, 30 mg of potassium carbonate(0.18 mmol) and 30 mg of 1-iodopropan (0.18 mmol) were added to the flask. Thereafter, the mixture was stirred at 85° C. for 12 hours. After the termination of the reaction is confirmed with thin layer chromatography, the reaction mixture was filtered to obtain the filtrate. The residue obtained by concentrating the filtrate was purified with silica gel column chromatography to prepare 23 mg of the title compound.

mp: 152–153° C.

R$_f$: 0.5 (Hexane:Ethylacetate=6:4)

¹H-NMR(CDCl₃/TMS) (ppm): δ 1.01 (t, 6H), 1.73–1.84 (m, 4H), 3.90 (t, 4H), 6.80–6.83 (dd, 4H), 7.48–7.51 (dd, 4H), 7.63 (s, 1H), 9.63 (s, 2H)

EXAMPLE 29~34

In the Example 28, alkylating agent containing $R_3$ shown in table 1 was used in place of 1-iodopropan, and the same procedure as the example 28 was accomplished.

EXAMPLE 29

2,3-bis-(4-isopropyloxy-benzylidene)succinaldehyde mp: 200~202° C.

Rf=0.45 (Hexane:Ethylacetate=6:4)

¹H-NMR(CDCl₃/TMS) (ppm): δ 1.31(d, 12H, CH₃—CH—CH₃), 4.53~4.57(m, 2H, CH₃—CH—CH₃), 6.79 (d, 4H), 7.49(d, 4H), 7.62(s, 2H, CH═C—), 9.62(s, 2H, CH═O)

EXAMPLE 30

2,3-bis-(4-valeryoxy-benzylidene)succinaldehyde mp: gel

Rf=0.25 (Hexane:Ethylacetate=7:3)

$^1$H-NMR(CDCl$_3$/TMS) (ppm): δ 0.96(t, 6H, CH$_2$—CH$_3$), 1.37~1.49(m, 4H, CH$_2$—CH$_3$), 1.64(1.77(m, 4H, CH$_2$—CH$_2$), 2.55(t, 4H, OCH$_2$—CH$_2$), 7.04(d, 4H), 7.52(d, 4H), 7.69(s, 2H, CH=C—), 9.66(s, 2H, CH=O)

EXAMPLE 31

2,3-bis-(4-benzyloxy-benzylidene)succinaldehyde mp: 119~120° C.

Rf=0.65 (Hexane:Ethylacetate=4:6)

$^1$H-NMR(CDCl$_3$/TMS) (ppm): δ 5.06(s, 4H, O—CH$_2$-ph), 6.89~7.54(m, 18H$_{arom}$), 7.64(s, 2H, CH=C—), 9.64(s, 2H, CH=O)

EXAMPLE 32

2,3-bis-(4-benzoyloxy-benzylidene)succinaldehyde mp: 207~208° C.

Rf=0.36 (Hexane:Ethylacetate=6:4)

$^1$H-NMR(CDCl$_3$/TMS) (ppm): δ 7.21~8.18(m, 18H$_{arom}$), 7.73(s, 2H, CH=C—), 9.69(s, 2H, CH=O)

EXAMPLE 33

2,3-bis-(4-(2-fluorobenzoyloxy)benzylidene)succinaldehyde mp: 197~199° C.

Rf=0.31 (Hexane:Ethylacetate=6:4)

$^1$H-NMR(CDCl$_3$/TMS) (ppm): δ 7.17~8.09(m, 16H$_{arom}$), 7.73(s, 2H, CH=C—), 9.69(s, 2H, CH=O)

EXAMPLE 34

2,3-bis-(4-(4-bromobenzoyloxy)benzylidene)succinaldehyde mp: 223~225° C.

Rf=0.35 (Hexane:Ethylacetate=6:4)

$^1$H-NMR(CDCl$_3$/TMS) (ppm): δ 7.19~8.03(m, 16H$_{arom}$), 7.72 (s, 2H, CH=C—), 9.69(s, 2H, CH=O)

EXAMPLE 35

2,3-bis-(2-(N-methylpiperazine)benzylidene)succinaldehyde

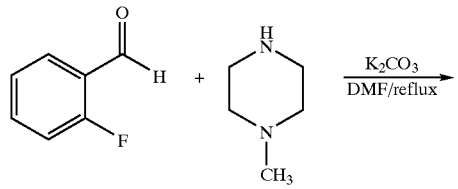

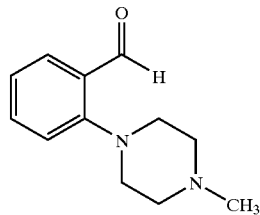

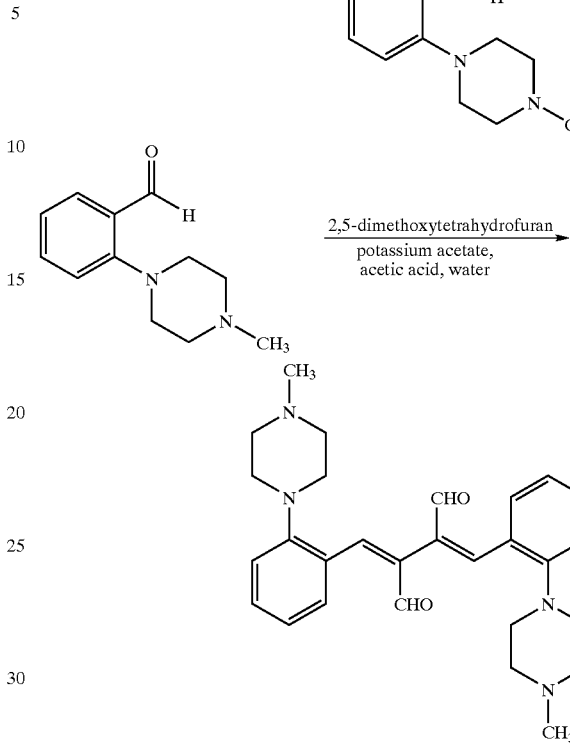

(Step 1): 2-(N-methylpiperazine)benzaldehyde 42.16 ml of 2-fluorobenzaldehyde (400 mmol) was added to the 250 ml round-bottomed flask, 100 ml of dimethylformamide(DMF) was further added therein. Thereafter, 8.28 g of potassium carbonate (60 mmol) and 44.4 ml of N-methylpiperazine (400 mmol) were added therein. The reaction mixture was refluxed at 150° C. for 10 hours.

After the reaction was terminated, the reaction mixture was cooled to the room temperature. Thereafter, 400 ml of water was added to the reaction mixture. The reaction mixture was extracted with 200 ml of ethyl acetate for three times. The ethyl acetate layers were collected, washed with water for three times and dried with anhydrous magnesium sulfate. The ethyl acetate was removed under reduced pressure. The resulting residue was purified with column chromatography, to give 2-(N-methylpiperazine)benzaldehyde.

(Step 2): Preparation of 2,3-bis-(2-(N-methylpiperazine)benzylidene)succinaldehyde 4.5 g of 2-(N-methylpiperazine)benzaldehyde (30 mmol) prepared in the above step was added to the 250 ml round-bottomed flask. Thereafter, 2 ml of 2,5-dimethoxytetrahydrofuran(15 mmol), 2 g of potassium acetate (20 mmol), 1 ml of acetic acid (16 mmol) and 1 ml of water were added to the flask. The reaction mixture was refluxed at 110° C. for 12 hours. After the reaction was terminated, the reaction mixture was cooled to the room temperature. Thereafter, water was added to the reaction mixture. The reaction mixture was extracted with 100 ml of chloroform for three times. The chloroform layers were collected, washed with water for three times and dried with anhydrous magnesium sulfate. The chloroform was removed under reduced pressure. The resulting residue was purified with column chromatography, to give the title compound as a yellow crystal (4.5 g, yield: 65%)

mp: 218~220° C.

$R_f$: 0.3 (CHCl$_3$:MeOH=8:2)

$^1$H-NMR(CDCl$_3$/TMS) (ppm): δ 2.25(s, 6H, OCH$_3$), 2.40~2.85(BRD, 16H, N—CH$_2$—CH$_2$—N), 6.94(dt, 2H, J=1.2, 7.5 Hz), 7.04(dd, 2H, 2H, J=1.2, 7.5 Hz), 7.22(dd, 2H, J=1.2, 7.8 Hz), 7.32(dt, 2H, J=1.2, 7.5 Hz), 7.92(s, 2H, CH=C—), 9.70(s, 2H, CH=O)

EXAMPLE 36~39

In the Example 1, benzaldehyde substituted with R$_1$, R$_2$ and R$_3$ shown in table 1 was used in place of benzaldehyde, and the same procedure as the example 1 was accomplished.

EXAMPLE 36

2,3-bis-(3-(4-chlorobenzyloxy)-benzylidene) succinaldehyde mp: 193~194° C.

$R_f$: 0.48 (Hexane:Ethylacetate=6:4)

$^1$H-NMR(CDCl$_3$/TMS) (ppm): δ 4.93(dd, 4H, CH$_2$-Arom), 6.96~7.32(m, 16H$_{arom}$), 7.55(s, 2H, CH=C—), 9.53(s, 2H, CH=O)

EXAMPLE 37

2,3-bis-(3-(4-methoxybenzyloxy)-benzylidene) succinaldehyde mp: 117~119° C.

$R_f$: 0.38 (Hexane:Ethylacetate=6:4)

$^1$H-NMR(CDCl$_3$/TMS) (ppm): δ 3.79(s, 6H, —OCH$_3$), 4.88(dd, 4H, CH$_2$-Arom), 6.85~7.27(m, 16H$_{arom}$), 7.57(s, 2H, CH=C—), 9.55(s, 2H, CH=O)

EXAMPLE 38

2,3-bis-(4-(4-chlorobenzyloxy)-benzylidene) succinaldehyde mp: 208~209° C.

$R_f$: 0.44 (Hexane:Ethylacetate=6:4)

$^1$H-NMR(CDCl$_3$/TMS)(ppm): δ 5.02(s, 4H, CH$_2$-Arom), 6.86~7.52(m, 16H$_{arom}$), 7.63(s, 2H, CH=C—), 9.63(s, 2H, CH=O)

EXAMPLE 39

2,3-bis-(4-(4-methoxybenzyloxy)-benzylidene) succinaldehyde mp: 218~220° C.

$R_f$: 0.25 (Hexane:Ethylacetate=6:4)

$^1$H-NMR(CDCl$_3$/TMS)(ppm): δ 3.81(s, 6H, —OCH$_3$), 4.97(s, 4H, CH$_2$-Arom), 6.88~7.52(m, 16H$_{arom}$), 7.63(s, 2H, CH=C—), 9.63(s, 2H, CH=O)

Cinnamaldehyde derivatives of the present invention prepared in the examples were shown in table 1.

TABLE 1

| No. | R$_1$ = R$_1$' (ortho) | R$_1$ = R$_1$' (meta) | R$_1$ = R$_1$' (para) | m.p. (° C.) |
|---|---|---|---|---|
| 1 | H | H | H | 150–151 |
| 2 | —F | H | H | 141–142 |
| 3 | —Cl | H | H | 177–178 |
| 4 | —Br | H | H | 194–195 |
| 5 | —OCH$_3$ | H | H | 163–164 |
| 6 | H | —Cl | H | 107–108 |
| 7 | H | —OCH$_3$ | —OH | 177–178 |
| 8 | H | —OCH$_3$ | —OCH$_3$ | 149–150 |
| 9 | H | H | —Cl | 172–173 |
| 10 | H | H | —OH | 244–246 |
| 11 | H | H | —CH$_3$ | 177–178 |
| 12 | H | H | —OCH$_3$ | 204–207 |
| 13 | —OCH$_2$CH$_2$CH$_3$ | H | H | 109–110 |
| 14 | —OCH$_2$CHCH$_2$ | H | H | 117–118 |
| 15 | —OCH(CH$_3$)$_2$ | H | H | 109–110 |
| 16 | —OCH$_2$C$_6$H$_5$ | H | H | 120–121 |
| 17 | —OCH$_2$C$_6$H$_4$-4-Cl | H | H | 186–187 |
| 18 | —OCH$_2$C$_6$H$_4$-4-Br | H | H | 210–211 |
| 19 | —OCH$_2$C$_6$H$_4$-4-NO$_2$ | H | H | 116–117 |
| 20 | H | —OCH$_2$CH$_2$CH$_3$ | H | 93–94 |
| 21 | H | —OCH(CH$_3$)$_2$ | H | 116–117 |
| 22 | H | —OCH$_2$C$_6$H$_5$ | H | 126–127 |
| 23 | H | —OCH$_3$ | —OCH$_2$CH$_2$CH$_3$ | 95–96 |
| 24 | H | —OCH$_3$ | —OCH(CH$_3$)$_2$ | 119–120 |
| 25 | H | —OCH$_3$ | —OCOCH$_3$ | 149–151 |
| 26 | H | —OCH$_3$ | —OCO(CH$_2$)$_3$CH$_3$ | gel |
| 27 | H | —OCH$_3$ | —OCOC$_6$H$_5$ | 107–110 |
| 28 | H | H | —OCH$_2$CH$_2$CH$_3$ | 152–153 |
| 29 | H | H | —OCH(CH$_3$)$_2$ | 200–202 |
| 30 | H | H | —OCO(CH$_2$)$_3$CH$_3$ | gel |
| 31 | H | H | —OCH$_2$C$_6$H$_5$ | 119–120 |
| 32 | H | H | —OCOC$_6$H$_5$ | 207–208 |
| 33 | H | H | —OCOC$_6$H$_4$-2-F | 197–199 |

TABLE 1-continued

| No. | R₁ = R₁' (ortho) | R₁ = R₁' (meta) | R₁ = R₁' (para) | m.p. (° C.) |
|---|---|---|---|---|
| 34 | H | H | —OCOC₆H₄-4-Br | 223–225 |
| 35 | N-methylpiperazine | H | H | 218–220 |
| 36 | H | —OCH₂C₆H₄-4-Cl | H | 193–194 |
| 37 | H | —OCH₂C₆H₄-4-OCH₃ | H | 117–119 |
| 38 | H | H | —OCH₂C₆H₄-4-Cl | 208–209 |
| 39 | H | H | —OCH₂C₆H₄-4-OCH₃ | 218–220 |

EXPERIMENTAL EXAMPLE 1

Cell Cycle Analysis

In order to confirm that the cinnamaldehyde derivatives of the present invention could regulate cell cycle, the present inventors performed the following experiment.

Colon cancer cell of human SW620(ATCC) or HCT116 (ATCC) was transferred to T25 flask(culture 7.5 ml) by RPMI1640 (Gibco/BR) medium or DMEM medium (Gibco/BR) containing 10% FBS (fetal bovine serum), respectively. Thereafter the cell was incubated for 12 hours at 37° C. in incubator. After the cell was incubated for 12 hours, 7.5 μl of DMSO was added to a culture used as control group, for the final concentration to be 0.1%. In order to use in experiment, samples of various concentrations were prepared by dissolving the cinnamaldehyde derivatives of the present invention in DMSO. 7.5 μl of the prepared samples was added to a culture used as experimental group. Cell of control or experimental group was incubated for 48 hours.

For cell cycle analysis, incubated cell was removed from medium. Thereafter the incubated cell was separated from the flask by trypsin. Thus the cell was centrifuged at 300 g for 5 min. The cell was washed with phosphate buffer solution (PBS) to remove the residue medium from the cell. 3 ml of ethanol (70%) was added to the cell. The cell was fixed by being positioned at −20° C. for 12 hours. The fixed cell was centrifuged at 300 g for 3 min and washed with the cold PBS for two times to remove residual ethanol. The cell solution prepared by adding 500 μl of PBS to the cell was well mixed to produce the homogeneous state. 100 μg/ml RNase A 50 μl was added to the cell solution, thereafter the resulting cell solution was positioned at 37° C. for 30 min. The chromosomal DNA was stained by further adding 1 mg/ml propidium iodide (soluble in PBS) thereto.

Distribution of cell cycle of 20,000 stained cells were measured by using Becton-Dickinson FACS caliber (San Jose, Calif., USA). Amounts of cells dividing to G1, S or G2/M of cell cycle was measured by using Becton-Dickinson Modifit cell cycle analysis program, resulted in percentage.

The results were shown in table 2.

HCT116 GI₅₀ (μM) and SW620 GI₅₀ (μM) mean to be the concentrations at which growth of HCT116 and SW620 colon cancer cell was inhibited to the 50%, respectively.

TABLE 2

| No. | HCT116 GI₅₀(μM) | SW620 GI₅₀(μM) | G2/M at 1 μM(%) SW620 | G2/M at 1 μM(%) HCT116 |
|---|---|---|---|---|
| 1 | 8.39 | 1.52 | 45 | 42 |
| 2 | 4.02 | 10.73 | 58 | 48 |
| 3 | 0.91 | 0.91 | 47 | 40 |
| 4 | 1.05 | 2.14 | 36 | 38 |
| 5 | 3.72 | 1.55 | 50 | 55 |
| 6 | 3.62 | 90.58 | 66 | 60 |
| 7 | 7.87 | 3.53 | 38 | 30 |
| 8 | 5.49 | 10.46 | 75 | 71 |
| 9 | 3.62 | 24.16 | 67 | 63 |
| 10 | 1.36 | 1.02 | 65 | 61 |
| 11 | 1.03 | 5.17 | 44 | 40 |
| 12 | 9.62 | 10.24 | 57 | 59 |
| 13 | 5.28 | 2.11 | 62 | 65 |
| 14 | 5.28 | 2.64 | 76 | 72 |
| 15 | 5.34 | 5.34 | 69 | 70 |
| 16 | 1.41 | 0.63 | 80 | 43 |
| 17 | 0.84 | 0.54 | 76 | 71 |
| 18 | 2.63 | 4.64 | 70 | 75 |
| 19 | 5.19 | 7.09 | 39 | 32 |
| 20 | 2.74 | 6.74 | 76 | 72 |
| 21 | 4.23 | 0.61 | 74 | 75 |
| 22 | 7.59 | 3.58 | 65 | 68 |
| 23 | 0.62 | 2.28 | 56 | 50 |
| 24 | 0.71 | 0.91 | 55 | 48 |
| 25 | 17.68 | 66.31 | 48 | 43 |
| 26 | 11.18 | 54.04 | 47 | 46 |
| 27 | 2.95 | 13.87 | 77 | 79 |
| 28 | 0.82 | 0.55 | 70 | 72 |
| 29 | 0.82 | 1.06 | 47 | 49 |
| 30 | 20.98 | 65.05 | 65 | 63 |
| 31 | 3.58 | 7.38 | 62 | 64 |
| 32 | 11.94 | 5.97 | 52 | 56 |
| 33 | 7.43 | 5.57 | 71 | 72 |
| 34 | 30.42 | 16.66 | 62 | 60 |
| 35 | 5.23 | 0.72 | 79 | 52 |
| 36 | 7.5 | 6.3 | 42 | 41 |
| 37 | 3.4 | 5.1 | 46 | 35 |
| 38 | 3.8 | 2.2 | 53 | 44 |
| 39 | 3.7 | 6.8 | 48 | 38 |

As shown in the table 2, from the analysis of cell cycle of colon carcinoma cell line SW620 or HCT116, in which the compound of the present invention was administered, the increase of the number of a cell was confirmed in G2/M stage. So, the compound of the present invention is believed to arrest the cell in the stage of G2/M selectively.

EXPERIMENTAL EXAMPLE 2

In order to confirm that the cinnamaldehyde derivatives of the present invention could inhibit the growth of cancer cell, the present inventors performed the following experiment.

SW620 or HCT116 as colon cancer cell was inoculated in 100 mm plate to the amount of 2×10⁶ cells. Then, cinnamaldehyde derivative of the present invention (compound 16 or compound 35) was added to the plate in the concentration of 1 μM. Thereafter, the colon cancer cell was incubated for 48 hours. Trypsin was added to the plate, to separate the colon cancer cell from the plate. And 5 ml of PBS (phosphate buffer solution) was added to the plate, to prepare the cell mixture. The cell mixture was centrifuged at 1,500 rpm for 5 min for two times, to remove trypsin from the mixture. The residue was washed with PBS for two times, thus the resulting supernatant was discarded. 1 ml of PBS and 3~5 ml of cool ethanol(70%) was added to the resulting residue. The cell was fixed by being positioned at −20° C. for 12 hours. The fixed cell was centrifuged at 1,500 rpm for 5 min and washed with the cool PBS for two times to remove residual ethanol. RNase(10 μg/ml) was added to the fixed cell, to remove RNA. And DNA of the fixed cell was dyed with PI(propidium iodide, 50 μg/ml). After the fixed cell was positioned at 37° C. for 30 min, cell cycles of 20,000 cells were measured by using Becton-Dickinson FACS caliber (San Jose, Calif., USA). And amount of cell dividing to G0–G1, S or G2/M of cell cycle was measured by using Becton-Dickinson Modifit cell cycle analysis program, resulted in percentage.

For control group, the same procedure was accomplished except that DMSO was used in place of the cinnamaldehyde derivative.

The results were shown in table 3.

TABLE 3

| Cell | Group | Con. | Amount of cell (%) | | |
| --- | --- | --- | --- | --- | --- |
| | | | G0–G1 | S | G2-M |
| HCT116 | Control | 1 μM | 34.22 | 44.63 | 24.16 |
| | Compound 16 | 1 μM | 22.36 | 34.35 | 43.29 |
| | Compound 35 | 1 μM | 15.52 | 32.37 | 52.11 |
| SW620 | Control | 1 μM | 47.45 | 39.57 | 12.97 |
| | Compound 16 | 1 μM | 6.64 | 13.15 | 80.21 |
| | Compound 35 | 1 μM | 8.74 | 12.73 | 78.53 |

As shown in table 3, the compound 16 and the compound 35 of the present invention held a cancer cell in the stage G2/M. So, the compounds of the present invention can be effectively used as an inhibitor of cancer cell growth or a regulator of cell cycle.

INDUSTRIAL APPLICABILITY

As explained hereinbefore, the compound of the present invention shown in the above formula 1 can be used as a cancer cell growth inhibitor or a cell cycle regulator since it can regulate the cell cycle by holding a cell in the middle of division in the stage G2/M and can inhibit the cancer cell growth thereby.

What is claimed is:

1. Cinnamaldehyde derivatives represented by formula 1:

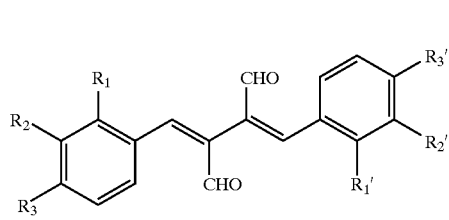

Formula 1 wherein $R_1$ and $R_1'$ are the same, $R_2$ and $R_2'$ are the same, and $R_3$ and $R_3'$ are the same, $R_1$, $R_2$ and $R_3$ are independently hydrogen, hydroxy, halogen, $C_1$~$C_4$ alkyl, $C_1$~$C_4$ alkoxy,

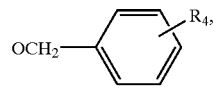

$OCOR_5$, or N-methylpiperazine, $R_4$ is hydrogen, nitro, or $C_1$~$C_4$ alkoxy, and $R_5$ is $C_1$~$C_4$ alkyl, phenyl, or phenyl substituted by halogen, with the proviso that $R_3$ is not hydrogen, methyl, methoxy or chloride when $R_1$ and $R_2$ are hydrogen.

2. Cinnamaldehyde derivatives as set forth in claim 1, the cinnamaldehyde derivative is selected from the group consisting of 1) 2,3-bis-(2-fluarobenzylidene)succinaldehyde;
2) 2,3-bis-(2-chlorobenzylidene)succinaldehyde;
3) 2,3-bis-(2-bromobenzylidene)succinaldehyde;
4) 2,3-bis-(2-methoxybenzylidene)succinaldehyde;
5) 2,3-bis-(3-chlorobenzylidene)succinaldehyde;
6) 2,3-bis-(4-hydroxy-3-methoxy-benzylidene) succinaldehyde;
7) 2,3-bis-(3,4-dimethoxybenzylidene)succinaldehyde;
8) 2,3-bis-(4-hydroxy-benzylidene)succinaldehyde;
9) 2,3-bis-(2-propyloxy-benzylidene)succinaldehyde;
10) 2,3-bis-(2-allyloxy-benzylidene)succinaldehyde;
11) 2,3-bis-(2-isopropyloxy-benzylidene)succinaldehyde;
12) 2,3-bis-(2-benzyloxy-benzylidene)succinaldehyde;
13) 2,3-bis-(2-(4-chlorobenzyloxy)-benzylidene) succinaldehyde;
14) 2,3-bis-(2-(4-bromobenzyloxy)-benzylidene) succinaldehyde;
15) 2,3-bis-(2-(4-nitrobenzyloxy)-benzylidene) succinaldehyde;
16) 2,3-bis-(3-propyloxy-benzylidene)succinaldehyde;
17) 2,3-bis-(3-isopropyloxy-benzylidene)succinaldehyde;
18) 2,3-bis-(3-benzyloxy-benzylidene)succinaldehyde;
19) 2,3-bis-(4-propyloxy-3-methoxy-benzylidene) succinaldehyde;
20) 2,3-bis-(4-isopropyloxy-3-methoxy-benzylidene) succinaldehyde;
21) 2,3-bis-(4-acetyloxy-3-methoxy-benzylidene) succinaldehyde;
22) 2,3-bis-(4-valeryloxy-3-methoxy-benzylidene) succinaldehyde;
23) 2,3-bis-(4-benzoyloxy-3-methoxy-benzylidene) succinaldehyde;
24) 2,3-bis-(4-propyloxy-benzylidene)succinaldehyde;
25) 2,3-bis-(4-isopropyloxy-benzylidene)succinaldehyde;
26) 2,3-bis-(4-valeryloxy-benzylidene)succinaldehyde;
27) 2,3-bis-(4-benzyloxy-benzylidene)succinaldehyde;
28) 2,3-bis-(4-benzoyloxy-benzylidene)succinaldehyde;
29) 2,3-bis-(4-(2-fluorobenzoyloxy)-benzylidene) succinaldehyde;
30) 2,3-bis-(4-(4-bromobenozyloxy)-benzylidene) succinaldehyde;
31) 2,3-bis-(2-(N-methylpiperazine)benzylidene) succinaldehyde;
32) 2,3-bis-(3-(4-chlorobenzyloxy)-benzylidene) succinaldehyde;
33) 2,3-bis-(3-(4-methoxybenzyloxy)-benzylidene) succinaldehyde;

34) 2,3-bis-(4-(4-chlorobenzyloxy)-benzylidene) succinaldehyde; and 35) 2,3-bis-(4-(4-methoxybenzyloxy)-benzylidene) succinaldehyde.

3. A method for the preparation of the cinnamaldehyde derivatives of claim 1 comprising, conducting a linear dimerization of a substituted benzaldehyde of the formula

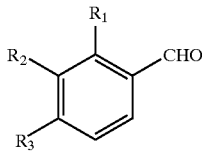

wherein $R_1$, $R_2$, and $R_3$ are independently hydrogen, hydroxyl, halogen, $C_1$–$C_4$ alkyl, $C_1$–$C_4$ alkoxy,

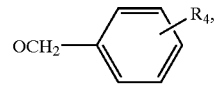

$OCOR_5$, or N-methylpiperazine, $R_4$ is hydrogen, nitro, or $C_1$–$C_4$ alkoxy, and $R_5$ is $C_1$–$C_4$ alkyl, phenyl, or phenyl substituted by halogen, with the proviso that $R_3$ is not hydrogen, methyl, methoxy, or chloride when $R_1$ and $R_2$ are hydrogen, in the presence of 2,5-dimethoxytetrhydrofuran, potassium acetate, acetic acid, and water.

4. A pharmaceutical composition for inhibiting growth of tumor cells comprising a cinnamaldehyde derivative of claim 1 as an effective ingredient.

5. A pharmaceutical composition for regulating cell cycle comprising a cinnamaldehyde derivative of claim 1 as an effective ingredient.

* * * * *